June 10, 1969 F. W. ANDERSON Plant Pat. 2,895
NECTARINE TREE
Filed Nov. 21, 1967
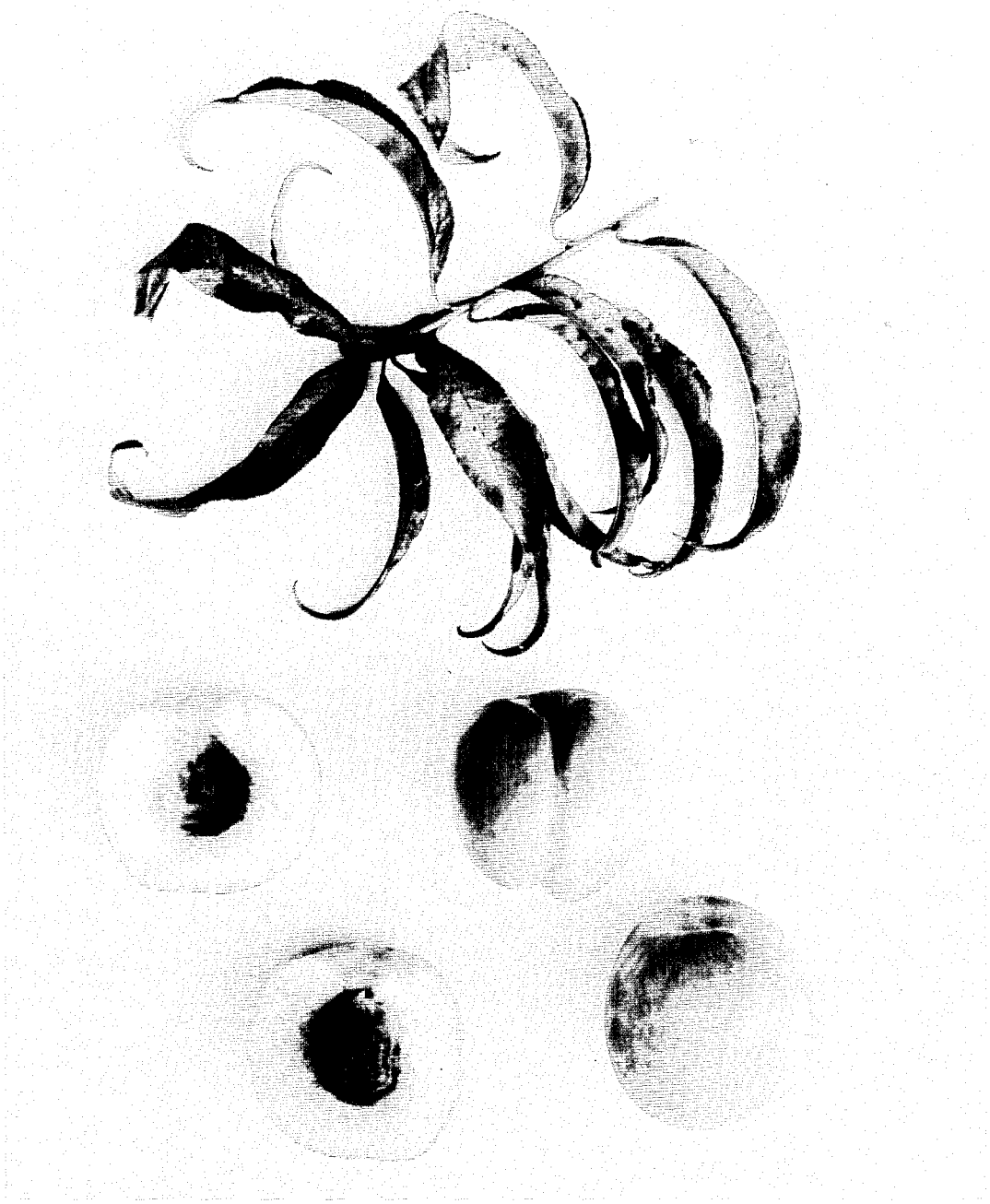
INVENTOR
Frederic W. Anderson
BY Webster & Webster
ATTORNEYS United States Patent Office Plant Pat. 2,895
Patented June 10, 1969

2,895
NECTARINE TREE

Frederic W. Anderson, Merced, Calif., assignor to Reedley Nursery, Inc., Reedley, Calif., a corporation of California Filed Nov. 21, 1967, Ser. No. 684,879
Int. Cl. A01h 5/08
U.S. Cl. Plt—41 1 Claim

ABSTRACT OF THE DISCLOSURE

A nectarine tree, of medium size and spreading in growth, which is a regular and productive bearer of large, uniform, globose, late season ripening clingstone fruit having yellow flesh, and yellow skin substantially overspread with bright red at maturity.

*Classification of the variety*

The present variety of nectarine tree is embraced by Group 123 of the classification established by Caillavet and Souty in their Monographie des Prinicpales Variétés de Pêchers, 1950 edition.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present variety of nectarine tree was originated by me, at my experimental nursery and orchard located as aforesaid; as a cross between the Red Grand nectarine (United States Plant Patent No. 1,060) and an unnamed seedling of the Gold King nectarine (United States Plant Patent No. 1,424). One seedling of such cross, and which is the present variety, evidenced—under continuing observation—certain desirable characteristics and was, therefore, selected for asexual reproduction, preparatory to commercialization.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

The herein claimed variety of nectarine tree—which is of medium size and spreading in growth—is a regular and productive bearer of large, unitform, globose, cling-stone fruit having yellow flesh, and yellow skin substantially overspread with bright red at maturity; the variety being particularly characterized by fruit having (1) a late season ripening period and (2) the smooth skin surface and bright red exterior coloring of the earlier ripening Red Grand nectarine. The present variety thus has the desirable skin texture and attractive coloring of the Red Grand, and which have not heretofore been present in a late ripening commercial nectarine.

The present variety of nectarine tree is further characterized by a late season ripening period which is immediately before the late ripening September Grand nectarine (United States Plant Patent No. 1,755).

*Brief description of the drawing*

The drawing is an illustration, by photographic reproduction in color, of a twig with leaves, and detached fruit; one fruit being cut in half to expose the flesh, and with the stone remaining in one cut half.

*Description of the variety*

The botanical details of this new and distinct variety of nectarine tree—with color definitions (except those in common color terms) referenced to Maerz and Paul Dictionary of Color—are as follows:

Tree:
- *Size.*—Medium.
- *Vigor.*—Medium.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Red to green.

Leaves:
- *Size.*—Medium. Average length—4⅞". Average width—1¼".
- *Form.*—Lanceolate.
- *Thickness.*—Medium.
- *Margin.*—Crenate.
- *Petiole.*—Medium length—average ½".
- *Glands.*—Average number and position—usually 2 on petiole, and 1 to 3 on blade. Medium size; reniform.
- *Color.*—Top side—medium to light Green (22–K–4). Under side—lighter Green (21–K–6).

Flower buds: *Size.*—medium.

Flowers:
- *Blooming period.*—Date of first bloom—Mar. 7, 1967. Date of full bloom—Mar. 24, 1967. Medium, as compared with other varieties.
- *Size.*—Large; showy.
- *Color.*—Pink.

Fruit:
- *Maturity when described.*—Eating ripe—Sept. 20, 1967.
- *Date of first picking.*—Sept. 10, 1967.
- *Date of last picking.*—Sept. 20, 1967.
- *Size.*—Uniform; large. Average diameter axially—2⅞". Average transversely in suture plane—2⅝".
- *Form.*—Uniform; symmetrical; globose.
- *Suture.*—Distinct; extends from base to apex with slight depression beyond pistil point.
- *Ventral surface.*—Rounded.
- *Cavity.*—Elongated in suture plane with suture showing on one side; medium depth.
- *Apex.*—Very short; depressed.
- *Pistil point.*—Absent.

Skin:

*Thickness.*—Medium.

*Texture.*—Smooth; tough.

*Tendency to crack.*—None.

*Down.*—Wanting.

*Color.*—Yellow (10–L–5) substantially overspread with bright Red (5–L–5), streaked and mottled shading to darker Red (7–L–6).

Flesh:

*Texture.*—Firm meaty.

*Ripens.*—Evenly.

*Flavor.*—Subacid.

*Aroma.*—Distinct to wanting.

*Eating quality.*—Good to best.

*Color.*—Yellow (11–L–4). Surface of pit cavity—Red (5–L–5) streaked into flesh.

Stone:

*Type.*—Cling; adheres to flesh over entire surface.

*Side.*—Large to medium. Average length—1¼″. Average breadth—1″. Average thickness—¾″.

*Form.*—Oblong to oval.

*Sides.*—Equal.

*Ridges.*—Rounded.

*Tendency to split.*—Slight.

*Color.*—Garnet Red (7–J–6).

Use: Market; dessert; long distance shipping.

Keeping quality: Good.

Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of nectarine tree, substantially as illustrated and described, which is of medium size, spreading in growth, and a regular and productive bearer of large, uniform, globose, clingstone fruit having yellow flesh, and yellow skin substantially overspread with bright red at maturity; the variety being particularly characterized by fruit having (1) a late season ripening period which is immediately ahead of the September Grand nectarine, and (2) the smooth skin surface and bright red exterior coloring of the earlier ripening Red Grand nectarine.

No references cited.

ROBERT E. BAGWILL, *Primary Examiner.*